(12) United States Patent  (10) Patent No.: US 7,527,965 B2
Ozil  (45) Date of Patent: May 5, 2009

(54) CELL CULTURE DEVICE

(75) Inventor: Jean-Pierre Ozil, Chaville (FR)

(73) Assignee: Institut National de la Recherche Agronomique, Paris (FR)

( * ) Notice: Subject to any disclaimer, the term of this patent is extended or adjusted under 35 U.S.C. 154(b) by 696 days.

(21) Appl. No.: 10/515,805

(22) PCT Filed: May 16, 2003

(86) PCT No.: PCT/FR03/01496

§ 371 (c)(1), (2), (4) Date: Nov. 19, 2004

(87) PCT Pub. No.: WO03/097787

PCT Pub. Date: Nov. 27, 2003

(65) Prior Publication Data

US 2005/0233441 A1    Oct. 20, 2005

(30) Foreign Application Priority Data

May 21, 2002  (FR)  .................................. 02 06185

(51) Int. Cl.
*C12M 1/12*  (2006.01)
*C12M 3/06*  (2006.01)
(52) U.S. Cl. ............... 435/295.3; 435/289.1; 435/309.1
(58) Field of Classification Search .... 435/289.1–309.1
See application file for complete search history.

(56) References Cited

U.S. PATENT DOCUMENTS 6,423,536 B1 *  7/2002  Jovanovich et al. ...... 435/287.2

FOREIGN PATENT DOCUMENTS

| DE | 199 48 473 |   | 4/2001 |
| WO | WO9113977 | * | 9/1991 |
| WO | WO 01 59447 |   | 8/2001 |

* cited by examiner

*Primary Examiner*—Walter D Griffin
*Assistant Examiner*—Shanta G Doe
(74) *Attorney, Agent, or Firm*—Blakely, Sokoloff, Taylor & Zafman LLP

(57) ABSTRACT

The invention relates to a device that is intended, in particular, for the culture of cells. The inventive device consists of a chamber (100) which is intended to receive the cells (10) and which comprises at least one liquid injection conduit (121, 122, 123, 124, 125, 126), the surface of the liquid contained in said chamber (100) being in free contact with the air. The invention is characterised in that it comprises a collector element (40) which can form at least one liquid bridge with the free surface of the liquid, said collector element (40) comprising a mouth piece (43) which is positioned essentially at the level of the free surface of the liquid contained in the chamber (100). The aforementioned mouth piece (43) is maintained at a vacuum such that it absorbs a flow of air which moves the surface film (30) of the liquid via the liquid bridge.

9 Claims, 2 Drawing Sheets

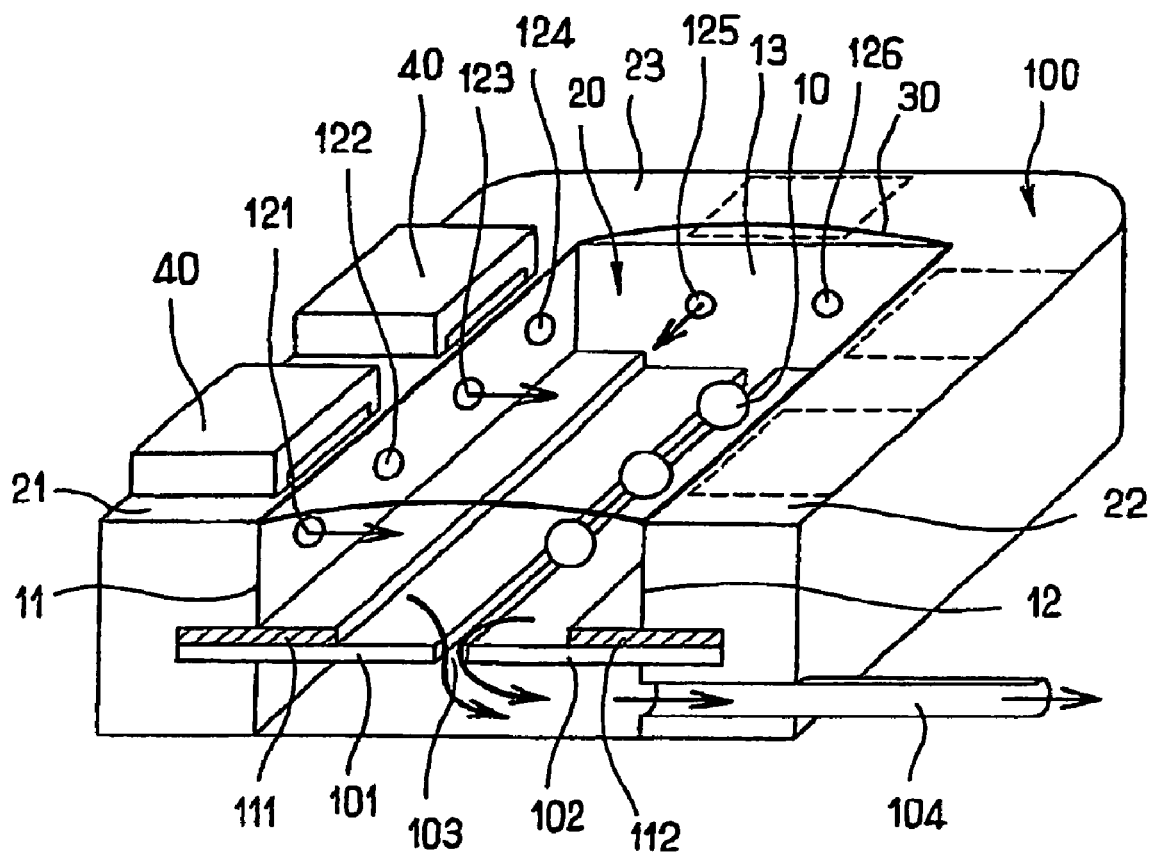
FIG_1

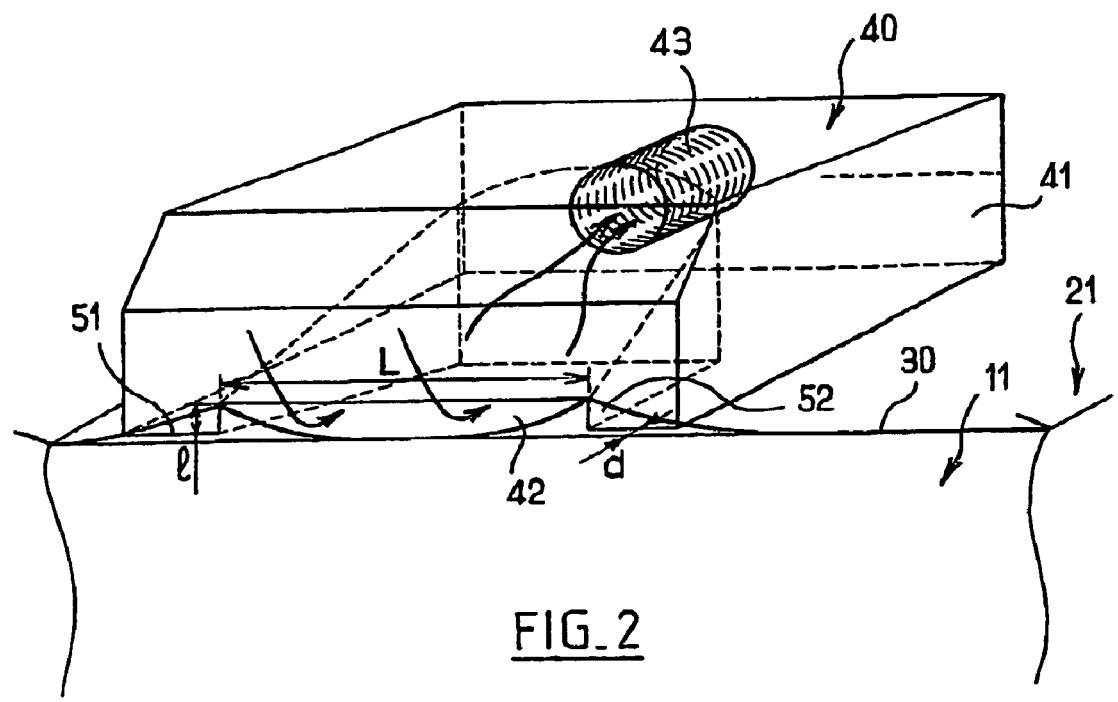
FIG_2
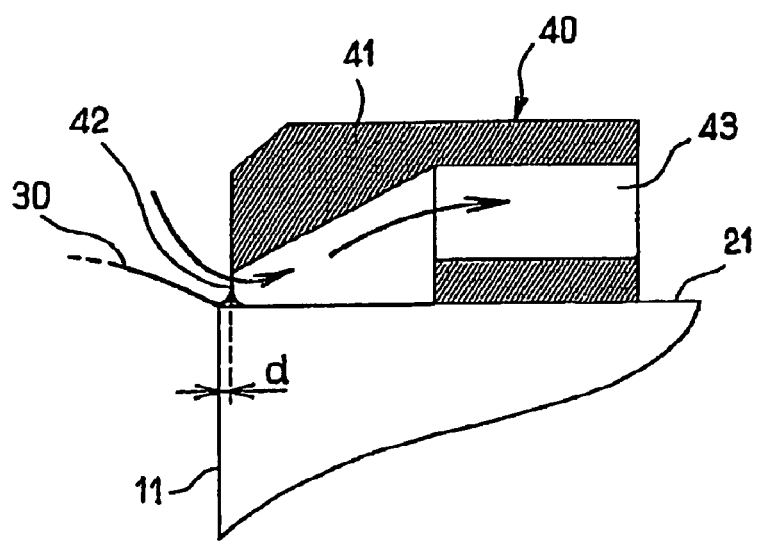
FIG_3

CELL CULTURE DEVICE

The present invention relates to a cell culture device which allows the treatment thereof with various media while avoiding the handling thereof.

Document FR 2 659 347 (published on Sep. 13, 1991) describes a cell culture device comprising a chamber intended to receive the cells. The chamber comprises a horizontal support formed by two glass plates that are juxtaposed and spaced apart so as to form between them a slot having a width which is less than the diameters of the cells. The cells to be treated are placed on the slot. This chamber is intended to contain liquid culture or pulse media. The various liquid media are injected successively into the chamber via distinct tubes placed above the wall supporting the cells. Part of the liquid contained that is injected into the chamber is evacuated by one or more tube(s) located below the wall. Another part of this liquid is evacuated by overflow.

In this device, the cells are held on the slot by virtue of the reduced pressure caused by the suction of the liquid medium by suction via the evacuation tube(s).

Such a device is intended in particular for culturing ovocytes, fertilized eggs or embryos, etc.

In particular, it can be used for activating experimental ovocytes, this activation being necessary for the correct subsequent development of the embryos. In order to cause this activation, a culture medium is injected into the chamber and the cells to be activated are placed in this culture medium. The ion-rich culture medium is then evacuated and simultaneously replaced with a pulse medium containing $Ca^{2+}$ ions. When the culture medium has been completely evacuated and replaced with the pulse medium, the cells are subjected to a pulse from an electric field, which causes the transient electropermeabilization of their plasma membrane and the penetration of the $Ca^{2+}$ ions into the cells. The pulse medium is then, in turn, evacuated and replaced with the culture medium. These steps are repeated a certain number of times such that the cells are subjected to a controlled series of calcium pulses which triggers their activation.

An advantage of this device is that it makes it possible to treat the cells with various media while avoiding the handling of the cells.

However, a problem posed by this type of device is that the replacing of one medium with another is relatively long, which limits the frequency of alternation of the media in the chamber.

For example, when the device is used for activating cells, a minimum time for injecting the pulse medium is necessary (of the order of 40 seconds) for replacing the culture medium with the pulse medium. This minimum time in fact guarantees sufficient washing of the cells by the pulse medium.

Should this minimum washing time not be observed, the pulse medium would contain residual ions originating from the culture medium. When the electric field was applied, these ions would induce a transmembrane ion current which could cause the cells to be destroyed.

Another problem related to the washing is that the prolonged exposure of the cells in the pulse medium having a low ionic strength disturbs the equilibrium of the cells and exposes them to deleterious effects. In order to preserve the cell survival, it is therefore necessary to reduce the washing time of the cells.

One aim of the invention is to provide a cell culture device which makes it possible to rapidly replace the medium in which the cells are placed.

It has been noted that evacuation of the liquid by overflow is a non-uniform phenomenon. In fact, during the injection of the liquid into the chamber, the free surface of the liquid rises above the upper plane of the enclosure such that the surface of the liquid takes the form of a convex meniscus. This phenomenon is related to the surface tensions which are exercised at the surface of the liquid and to the wettability of the vertical walls of the enclosure with this liquid. The difference in level of the liquid above the edges of the enclosure must reach a critical value in order for the equilibrium between, firstly, the forces related to the surface tensions and, secondly, the forces related to gravity to be broken. This break results in the surplus liquid flowing over the walls of the enclosure.

It results therefrom that the evacuation of the liquid by overflow occurs in a discontinuous and unpredictable manner. In particular, it may be that, during a phase of replacement of one medium with another, the medium to be replaced is not evacuated. This evacuation is not therefore satisfactory since it does not guarantee the washing of the cells during this replacement phase.

Moreover, another problem is that this discontinuous flow generates a succession of shockwaves in the liquid. These shockwaves move the cells on the support.

The cells have a tendency to move along the slot of the support element toward the center of the enclosure, where they come together. They are compressed against one another. The decrease in space between the cells modifies the efficiency of the washing at the periphery of each cell.

Finally, yet another problem is that the interface between the culture medium and the surrounding gas is the site of surface phenomena. Atomic or molecular films form at the free surface of the liquid. These films are not renewed when one medium is replaced with another in the chamber.

When the culture device is used for applying electric field pulses to the cells, the films can constitute conductivity bridges between the electrodes. These conductivity bridges establish a short circuit between the electrodes. As a result of this, there is a significant decrease in the effectiveness of the electric field applied.

To overcome these drawbacks, the invention proposes a device intended in particular for culturing cells, comprising a chamber intended to receive the cells, said chamber comprising at least one liquid injection conduit, the surface of the liquid contained in the chamber being in free contact with the air, characterized in that it comprises a collector element which can form at least one liquid bridge with the free surface of the liquid, the collector element comprising a mouthpiece which is placed substantially at the level of the free surface of the liquid contained in the chamber, the mouthpiece being kept at low pressure such that it absorbs a flow of air which moves the surface film of the liquid via the liquid bridge.

The device of the invention makes it possible to create a liquid bridge in the form of a meniscus between the free surface of the liquid and the collector element. This meniscus regulates, by means of an equilibrium effect, the surface tensions at the surface of the liquid contained in the chamber.

Such a device makes it possible, by virtue of the flow of air, to continuously eliminate the surplus liquid in the chamber and thus to maintain a constant level of liquid.

It also makes it possible to obtain a permanent renewal of the surface film of the liquid of the chamber.

In one embodiment of the invention, the collector element is placed on a rim of a wall of the chamber, its mouthpiece being set back from the wall.

Preferably, a portion of the rim located in front of the mouthpiece of the collector element is covered with a hydrophilic substance.

Preferably, the mouthpiece is set back from the wall at a distance d of between 10 and 30 µm.

Preferably, the mouthpiece of the collector is elongated in shape and extends longitudinally along the edge of the wall.

In one embodiment of the invention, the opening is of the order of 2 to 4 mm in length.

In one embodiment of the invention, the opening is of the order of 0.15 to 0.30 mm in height.

In one embodiment of the invention, the mouthpiece of the collector element has a generally rectangular shape.

Advantageously, the device comprises several elements placed along the edges of the walls of the chamber.

The invention also relates to a method for regulating the level of a liquid contained in a chamber intended to receive cells, said chamber comprising at least one liquid injection conduit, the surface of the liquid contained in the chamber being in free contact with the air, characterized in that at least one liquid bridge is formed with the free surface of the liquid and a flow of air is drawn by suction in the vicinity of the liquid bridge, such that this flow of air moves the surface film of the liquid via the liquid bridge.

Other characteristics and advantages will further emerge from the following description, which is given purely by way of non-limiting illustration and should be read with regard to the attached figures, among which:

FIG. 1 is a representative diagram of an example of a cell culture device in accordance with an embodiment of the invention, FIG. 2 is a detailed diagram of a collector of the device in FIG. 1, FIG. 3 is a sectional diagram of the collector in FIG. 2.

In FIG. 1, the cell culture device represented comprises a chamber 100 comprising walls 11, 12 and 13 delimiting an enclosure 20 intended to contain a liquid medium. The enclosure is filled with a liquid medium corresponding to the ongoing cell treatment phase. In enclosure 20, a horizontal support element is positioned, formed by the juxtaposition of two glass plates 101 and 102. The glass plates 101 and 102 are held embedded in the side walls 11 and 12 of the chamber. These glass plates 101 and 102 are set apart so as to define between them a rectilinear slot 103 having a width that is less than the diameter of the ovocytes 10 intended to be treated.

The chamber 100 also comprises electrodes 111 and 112 which extend longitudinally on either side of the slot 103.

The culture liquid is brought to the upper part of the enclosure 20 by a series of conduits, the mouthpieces 121, 122, 123, 124, 125 and 126 of which are placed at regular intervals along the walls 11, 12 and 13. Moreover, a part of the liquid contained in the chamber is evacuated by means of an evacuation conduit 104 located at a level lower than that of the support element. The stream of liquid keeps the ovocytes 10 stuck to the slot 103 by means of low pressure.

The free surface of the liquid contained in the chamber 100 forms a molecular film 30 which is convex in shape. This film 30 consists of an alignment of oriented molecules, the hydrophilic function of which positions itself toward the fluid and the hydrophobic portion of which positions itself toward the outer air.

In order to eliminate the molecular film 30 and to absorb the surplus liquid contained in the enclosure 20, the culture device comprises collectors 40 placed on a horizontal rim 21 of the wall 11 of the enclosure 20.

In a symmetrical manner, the device may comprise collectors placed on rims 22 or 23 of the walls 12 or 13 (at the positions represented by dashed lines).

These collectors 40 may be placed at regular intervals around the enclosure 20.

FIG. 2 is a diagram representing in greater detail a collector 40 of the cell culture device in FIG. 1.

This collector 40 is placed on the rim 21 of the wall 11 of the chamber, set back from this wall by a distance d. It comprises a hollow body 41 which has a rectangular opening 42 extending along the wall 11. This opening has a length of L=2 mm and a height of l=0.2 mm.

Two liquid bridges 51 and 52 are formed between the surface 30 of the liquid contained in the enclosure 20 and the vertical edges of the opening 42. These liquid bridges 51 and 52 are formed by distortions of the surface 30 of the liquid (or menisci) in contact with the edges of the opening 42.

The collector 40 comprises, moreover, an evacuation conduit 43 connected to a suction device, which is not represented. This suction device makes it possible to draw by suction the air contained in the collector 40. This suction causes air to circulate through the opening 42, which moves an upper portion of the liquid contained in the chamber via the liquid bridges 51 and 52. As a result of this, the molecular film 30 at the surface of the liquid is permanently moved by the air circulating in the collector and eliminated from the surface of the liquid.

The length L of the opening was chosen so as to be at least twice the capillary length $k^{-1}$ of the liquid contained in the chamber. This characteristic guarantees the formation of two lateral menisci and therefore the non-sealing of the opening 42 by the liquid. The air is therefore always free to circulate through the opening 42.

The liquids generally used for treating the cells generally have capillary lengths of between 1 mm and 2 mm. The length L of the opening will therefore preferably be of the order of 2 to 4 mm.

The collector 40 is set back from the wall by a distance d. In fact, the opening should not be too close to the wall 11, since, in this case, the capillarity forces would result in the formation of a single liquid bridge which would seal the opening 42 and which would empty out of the enclosure 20 the liquid that it contains.

However, the opening 42 should not be too far from the wall 11, since, in this case, the collector would no longer have any effect on the liquid.

Moreover, a distance d of a few microns results in the formation of a concave meniscus. Now, the concave shape has several drawbacks:

firstly, it increases surface tensions toward the bottom of the enclosure 20, in the vicinity of the cells 10, which makes it more delicate for the operator to position or remove the cells, secondly, the concave shape modifies the optical path of the light and makes it more difficult for the operator to see the cells.

Consequently, it is desirable to maintain a meniscus with a stable convex shape. For this reason, the distance d is preferably between 10 and 30 μm.

Thus, in the collector 40 represented in FIG. 2, the distance d is 20 μm.

Preferably, the rims 21, 22 and 23 of the walls 11, 12 and 13 of the chamber are covered with a hydrophobic substance, except in front of the openings 42 of the collectors, where they are covered with a hydrophilic substance. This arrangement promotes the initiation of a liquid bridge at the level of the collectors 40.

In FIG. 3, a collector 40 is shown in the form of a section along the evacuation conduit 43. The path of the air drawn by suction is represented by arrows.

The invention claimed is:

1. A device for culturing cells, comprising:
  a chamber to receive the cells, said chamber comprising at least one liquid injection conduit, a surface of the liquid contained in the chamber being in free contact with the air, characterized in that it comprises a collector element which can form at least one liquid bridge with the free surface of the liquid, the collector element comprising a mouthpiece which is placed substantially at the level of the free surface of the liquid contained in the chamber, the mouthpiece being kept at low pressure such that it absorbs a flow of air which moves the surface film of the liquid via the liquid bridge.

2. The device of claim 1, wherein the collector element is placed on a rim of a wall of the chamber and the mouthpiece is set back from the wall.

3. The device of claim 2, wherein a portion of the rim located in front of the mouthpiece of the collector element is covered with a hydrophilic substance.

4. The device of claim 2 or 3, wherein the mouthpiece is set back from the wall at a distance (d) of between 10 and 30 μm.

5. The device of claim 1, wherein the mouthpiece of the collector element is elongated in shape and extends longitudinally along the edge of the wall.

6. The device of claim 5, wherein the opening has a length of 2 to 4 mm.

7. The device of claim 5, wherein the opening has a height of 0.15 to 0.30 mm.

8. The device of claim 1, wherein the mouthpiece has a generally rectangular shape.

9. The device of claim 1, further comprising:
 a plurality of collector elements placed along the edges of the walls of the chamber.

* * * * *